United States Patent [19]
Frid

[11] Patent Number: 5,849,037
[45] Date of Patent: Dec. 15, 1998

[54] SELF-EXPANDING STENT FOR A MEDICAL DEVICE TO BE INTRODUCED INTO A CAVITY OF A BODY, AND METHOD FOR ITS PREPARATION

[75] Inventor: Noureddine Frid, Beersel, Belgium

[73] Assignee: Corvita Corporation, Miami, Fla.

[21] Appl. No.: 626,932

[22] Filed: Apr. 3, 1996

[30]     Foreign Application Priority Data

Apr. 12, 1995 [BE] Belgium ............................. 09500334

[51] Int. Cl.⁶ ..................................................... A61F 2/06
[52] U.S. Cl. .............................................. 623/1; 606/195
[58] Field of Search .................................. 623/1, 11, 12; 606/194, 195, 198

[56]        References Cited

U.S. PATENT DOCUMENTS

| | | | |
|---|---|---|---|
| 1,920,495 | 8/1933 | Brown et al. ................................ | 140/7 |
| 2,836,181 | 5/1958 | Tapp ........................................ | 128/334 |
| 2,977,839 | 4/1961 | Koch ............................................ | 87/1 |
| 3,095,017 | 6/1963 | Bleiler et al. ............................ | 139/387 |
| 3,105,492 | 10/1963 | Jeckel ....................................... | 128/334 |
| 3,272,204 | 9/1966 | Artandi et al. .......................... | 128/334 |
| 3,304,557 | 2/1967 | Polansky ........................................ | 3/1 |
| 3,317,924 | 5/1967 | Le Veen et al. .................................. | 3/1 |
| 3,463,158 | 8/1969 | Schmitt et al. .......................... | 128/334 |
| 3,479,670 | 11/1969 | Medell ............................................ | 3/1 |
| 3,485,234 | 12/1969 | Stevens ....................................... | 128/2 |
| 3,509,883 | 5/1970 | Diebelius ............................... | 128/348 |
| 3,526,906 | 9/1970 | De Laszlo ..................................... | 3/1 |
| 3,562,820 | 2/1971 | Braun ............................................ | 3/1 |
| 3,580,289 | 5/1971 | James, Jr. ............................... | 138/121 |
| 3,585,707 | 6/1971 | Stevens ..................................... | 29/427 |
| 3,626,947 | 12/1971 | Sparks ................................. | 128/334 R |
| 3,710,777 | 1/1973 | Sparks ..................................... | 128/1 R |
| 3,730,835 | 5/1973 | Leeper .................................... | 195/1.7 |
| 3,822,238 | 7/1974 | Blair et al. ................................ | 260/75 |

(List continued on next page.)

FOREIGN PATENT DOCUMENTS

| | | |
|---|---|---|
| 0 587 197 | 10/1991 | European Pat. Off. . |
| 06121015A1 | 10/1994 | European Pat. Off. . |
| 0621015 | 10/1994 | European Pat. Off. .................... 623/1 |
| 1 602 513 | 1/1970 | France . |
| 30 19 996 | 12/1981 | Germany . |
| 1 205 743 | 9/1970 | United Kingdom . |
| 2 015 118 | 9/1979 | United Kingdom . |
| 2 033 233 | 5/1980 | United Kingdom . |
| 2 077 107 | 12/1981 | United Kingdom . |
| 2 135 585 | 3/1986 | United Kingdom . |
| WO88/00813 | 2/1988 | WIPO . |
| 9112779 | 9/1991 | WIPO ....................................... 623/1 |
| WO91/12779 | 9/1991 | WIPO . |
| WO94/24961 | 11/1994 | WIPO . |

OTHER PUBLICATIONS

"A Study of the Geometrical and Mechanical Properties of a Self–Expanding Metallic Stent . . . " Jedwab et al, Jour. of Applied Biomaterials, Vo. 4, pp. 77–85 1993.

"Oesophageal Strictures" Didcott, Annals of the Royal Cllege of Surgeons of England, vol. 55, pp. 112–126, Aug. 1973.

*Primary Examiner*—Debra S. Brittingham
*Attorney, Agent, or Firm*—David P. Gordon; David S. Jacobson; Thomas A. Gallagher

[57]        ABSTRACT

A self-expanding stent for a medical device to be introduced into a cavity of a human body, is disclosed and includes a radially expandable and axially retractable tubular body (1), characterized in that the tubular body comprises first filaments (2, 3) which are arranged side by side in a number at least equal to two, wound along a first helicoid direction around a longitudinal axis (4) of the tubular body, and second flexible rigid filaments (5, 6) which are arranged side by side in a number at least equal to two, wound along a second helicoid direction opposite to the first, each multiple filament wound in one of the said directions crossing multiple filaments wound in the other direction according to a plaited arrangement. Methods for reproducibly forming the stent of the invention are disclosed.

10 Claims, 3 Drawing Sheets

U.S. PATENT DOCUMENTS

| | | | |
|---|---|---|---|
| 3,868,956 | 3/1975 | Alfidi et al. | 128/345 |
| 3,878,565 | 4/1975 | Sauvage | 3/1 |
| 3,929,126 | 12/1975 | Corsaut | 128/240 |
| 3,974,526 | 8/1976 | Dardik et al. | 3/1.4 |
| 3,993,078 | 11/1976 | Bergentz et al. | 128/334 R |
| 4,044,404 | 8/1977 | Martin et al. | 3/19 |
| 4,086,665 | 5/1978 | Poirier | 3/1.4 |
| 4,106,129 | 8/1978 | Carpentier et al. | 3/1.5 |
| 4,130,904 | 12/1978 | Whalen | 3/1.4 |
| 4,134,402 | 1/1979 | Mahurkar | 128/214 R |
| 4,140,126 | 2/1979 | Choudhury . | |
| 4,164,045 | 8/1979 | Bokros et al. | 3/1.4 |
| 4,173,689 | 11/1979 | Lyman et al. | 521/64 |
| 4,193,138 | 3/1980 | Okita | 3/1.4 |
| 4,323,071 | 4/1982 | Simpson et al. | 128/343 |
| 4,355,426 | 10/1982 | MacGregor | 3/1.4 |
| 4,441,215 | 4/1984 | Kaster | 3/1.4 |
| 4,459,252 | 7/1984 | MacGregor | 264/46.9 |
| 4,475,972 | 10/1984 | Wong | 156/167 |
| 4,503,569 | 3/1985 | Dotter | 3/1.4 |
| 4,583,968 | 4/1986 | Mahurkar | 604/43 |
| 4,610,688 | 9/1986 | Silvestrini et al. | 623/1 |
| 4,655,771 | 4/1987 | Wallsten | 623/1 |
| 4,692,141 | 9/1987 | Mahurkar | 604/43 |
| 4,731,073 | 3/1988 | Robinson | 623/1 |
| 4,743,251 | 5/1988 | Barra | 623/1 |
| 4,787,899 | 11/1988 | Lazarus | 623/1 |
| 4,850,999 | 7/1989 | Planck | 623/1 |
| 4,871,357 | 10/1989 | Hsu | 604/266 |
| 4,875,480 | 10/1989 | Imbert | 128/343 |
| 4,878,906 | 11/1989 | Lindemann et al. | 623/1 |
| 4,895,561 | 1/1990 | Mahurkar | 604/43 |
| 4,935,006 | 6/1990 | Hasson | 604/43 |
| 4,954,126 | 9/1990 | Wallsten | 606/36 |
| 5,026,377 | 6/1991 | Burton et al. | 606/108 |
| 5,061,275 | 10/1991 | Wallsten et al. | 623/1 |
| 5,064,435 | 11/1991 | Porter | 623/12 |
| 5,078,720 | 1/1992 | Burton et al. | 606/108 |
| 5,116,360 | 5/1992 | Pinchuk et al. | 623/1 |
| 5,160,341 | 11/1992 | Brenneman et al. | 606/198 |
| 5,188,593 | 2/1993 | Martin | 604/43 |
| 5,197,978 | 3/1993 | Hess | 623/1 |
| 5,201,757 | 4/1993 | Heyn et al. | 606/198 |
| 5,235,966 | 8/1993 | Jamner | 128/20 |
| 5,242,399 | 9/1993 | Lau et al. | 604/104 |
| 5,279,561 | 1/1994 | Roucher et al. | 604/96 |
| 5,290,295 | 3/1994 | Querals et al. | 606/108 |
| 5,312,415 | 5/1994 | Palermo | 606/108 |
| 5,330,500 | 7/1994 | Song | 606/198 |
| 5,360,397 | 11/1994 | Pinchuk | 604/27 |
| 5,383,892 | 1/1995 | Cardon et al. | 606/198 |
| 5,395,390 | 3/1995 | Simon et al. | 606/198 |
| 5,397,355 | 3/1995 | Marin et al. | 623/12 |
| 5,405,378 | 4/1995 | Strecker | 623/1 |
| 5,415,664 | 5/1995 | Pinchuk | 606/108 |
| 5,433,723 | 7/1995 | Lindenberg et al. | 606/198 |
| 5,545,208 | 8/1996 | Wolff et al. | 623/1 |

SELF-EXPANDING STENT FOR A MEDICAL DEVICE TO BE INTRODUCED INTO A CAVITY OF A BODY, AND METHOD FOR ITS PREPARATION

This invention is related to co-owned U.S. Ser. No. (Docket #COR-008) filed on even date herewith and claiming priority from Belgium application 09500335, which are hereby incorporated by reference herein in their entireties.

BACKGROUND OF THE INVENTION

1. Field of the Invention

The present invention relates to a self-expanding stent for a medical device to be introduced into a cavity of a human or animal body. More particularly, the present invention relates to a braided or woven filament medical stent having a tubular body which is radially expandable and retractable between a first diameter, corresponding to a compressed state of the stent, and a second diameter, greater than the first, corresponding to a resting state of the stent, and is axially expansible and retractable between a first length, corresponding to the working state, and a second length, less than the first, corresponding to the resting state. For purposes herein, the term "self-expanding stent" is intended to mean that, when brought into its working position (i.e., a radially compressed and axially extended position), the stent, once released, tends spontaneously to substantially recover its resting position (i.e., a radially expanded and axially contracted position). Also, the term "medical device to be introduced into a cavity of a human or animal body" as used herein should be taken to mean, for example, luminal endoprostheses, catheters, dilators, grafts and the like which can be introduced, for example, into the vascular, esophageal, urinary, urethral, or biliary cavities and other tubular ducts of the body. Further, the terms "woven", "braided" and "plaited" are used interchangeably herein and are intended to be understood in their broadest sense to require an over-under interlacing of a plurality of filaments.

2. State of the Art

Braided or woven filament medical stents which are used as vascular, esophageal or other dilators have been known for a long time (See, e.g., GB-1,205,743). These stents, formed by a tubular plaited structure of individual filaments include, in the resting state, filaments forming a fairly small angle with respect to a longitudinal axis of the tube (e.g., 30°). Stents with a relatively small directed angle do not offer a sufficient capacity for radial expansion when they are released after having been radially compressed. Their crushing resistance is also insufficient when they are used in cavities of the body whose walls exert a strong radial pressure on the stent introduced.

It has consequently been sought to overcome these drawbacks by providing a plaited structure of individual filaments with a larger angle so that, in the resting state of the stent, the filaments exhibit an angle greater than 45°, preferably of at least 60°, with respect to a longitudinal axis of the stent (See, e.g., U.S. Pat. No. 4,655,711 and U.S. Pat. No. 4,954,126). However, stents with a large braiding angle have a great drawback. Indeed, the tubular stent must be extended to two to three times its initial length in order to be capable of being inserted in a vascular introducer. It then occupies from 40 to 50% of the length of the introducer, and stiffens it and renders it difficult to pass through the femoral artery through which introduction into the body is generally initiated. On release, the tubular structure retracts by two to three times in length. It is therefore very difficult to estimate the length which will be deployed in the internal cavity of the body treated. This may lead to serious problems, as it is difficult to estimate the exact location where the stent will be anchored. For example, a length of stent may be deployed beyond a vascular bifurcation and thus lead to undesirable artery closure when the stent is provided with a covering, as is the case for luminal endoprostheses. In another case, if the deployed length is too short, the aneurysm treated will not be closed. Finally, it has been observed that stents with a large plaiting angle do not exhibit good resistance to blood pressure inside the aneurysms treated.

Other filament-based tubular plaited structures, which are used in devices to be introduced into the human body, are also described, in particular, in Patent #EP-A-0,183,372, U.S. Pat. No. 3,509,883, U.S. Pat. No. 5,061,275 and U.S. Pat. No. 5,171,262.

SUMMARY OF THE INVENTION

According to the invention, the problems mentioned hereinabove have been solved by an self-expanding stent as described at the outset, in which the tubular body comprises first filaments which are arranged side by side in a number at least equal to two and thus form first multiple filaments wound along a first helicoid direction around a longitudinal axis of the tubular body, and second filaments which are arranged side by side in a number at least equal to two and thus form second multiple filaments wound along a second helicoid direction opposite to the first, each multiple filament wound in one of the said helicoid directions crossing multiple filaments wound in the other helicoid direction according to a plaited arrangement. Such a stent exhibits high dimensional and geometrical stability, without requiring a large Plaiting angle and the accuracy on release of this stent is therefore greatly increased.

In the braided or woven arrangement of the filaments, in some embodiments, a first multiple filament will, when crossing over with a second multiple filament, pass above the latter and, during the subsequent cross-over, pass below the second filament then crossed, and so on. In other embodiments, the first multiple filament passes above a second multiple filament having two or more successive cross-overs and will then only pass below a second multiple filament after a plurality of successive cross-overs, and so on. Mixed plaited arrangements (e.g., two over, one under) may also be provided, as can plaited structures formed partially of double filaments and monofilaments.

According to a particular form of the invention, the tubular body formed by plaited multiple filaments has at least at one of its ends, in the resting state, a flaring in which the multiple filaments follow a helix with increasing radii. Such an embodiment is particularly advantageous for treating, for example, aortic aneurysms in which contraction of the proximal or distal neck of the aneurysm occurs. The stent according to the invention, and in particular at its flared end, resists crushing by the arterial wall due to contraction of the neck. The radial expansion of the flared part of the stent furthermore promotes the absence of migration along the wall of the cavity in which it is to be applied and applies leakproofness to the distal neck of the aneurysm.

According to one highly advantageous embodiment of the invention, the ends of the stent are flared so that the stent assumes the shape of a hyperboloid. As will be discussed hereinafter, this embodiment has the great advantage of very simple manufacture and perfect reproducibility of the plaiting angle.

According to another aspect of the invention, in the resting state, the tubular body includes multiple filaments oriented at an angle equal to, and preferably less than 45° with respect to the longitudinal axis of the stent. According to the invention, the plaiting angle need not be high in order to obtain good dimensional stability properties. A significant improvement in the release of the stent in the cavity in which it is to be applied consequently results.

According to another advantageous embodiment of the invention, a stent-graft is provided with an expandable covering applied to at least one of an external wall surface and an internal wall surface of the stent body. Such a covering may be applied onto the stent using any known technique, for example in accordance with the teaching of Patent #EP-A-0,603,959. This makes it possible to form, for example, luminal endoprostheses with a diameter of 40 mm when resting, the covering of which is made of polycarbonate-urethane or other fibers with a fiber diameter of 5–25 μm. The diameters of such endoprostheses may then be reduced to a diameter of 4 to 5 mm for insertion in an introducer. The graft covering may take many forms and may be produced using other well-known techniques without departing from the scope of the invention.

The invention also provides a method for preparing a self-expanding stent for a medical device to be introduced into a cavity of a body, comprising plaiting filaments originating from interposed reels rotating in opposite directions so as to form a tubular body which is radially expansible and retractable between a first diameter, corresponding to a compressed state of the stent, and a second diameter, greater than the first, corresponding to a resting state of the stent. The stent is axially expansible and retractable between a first length, corresponding to the compressed state, and a second length, less than the first, corresponding to the resting state.

It has for a long time been known in the field of cable production to manufacture tubular plaited structures formed by metallic filaments. The problems to be solved in the field of stents however, are completely different, and the requirements imposed on the plaited structures in cable production are entirely separate. On the other hand, methods for plaiting a self-expanding stent are also known, such as described in U.S. Pat. No. 5,061,275. However, the methods of manufacture of the art do not reliably obtain reproducible results.

According to the present invention, a method of forming a stent comprises, prior to plaiting, winding at least some of the reels with multiple filaments, also referred to as multiple ends, arranged side by side. The plaiting comprises winding first multiple filaments along a first helicoid direction around a longitudinal axis of the tubular body and winding second multiple filaments along a second helicoid direction opposite to the first, each multiple filament wound in one of the helicoid directions crossing multiple filaments wound in the other helicoid direction in an over-under manner. Such a method makes it possible to manufacture a stent with much better performance than those of the prior art, without needing to modify the existing equipment and therefore without additional investment.

According to another aspect of the invention, the tubular stent body is plaited to provide a diameter greater than the desired resting diameter. The plaited tubular body is then expanded by its introduction into a tube having an internal diameter substantially corresponding to the desired resting diameter. The stent is then thermally treated in order to set and fix the axially extended tubular body so that after this treatment, it is in the resting state. Alternately, the braided tubular structure can be secured over a mandrel and heat treated in this configuration to approximate the resting diameter of the stent. This embodiment makes it possible to obtain angles between the filaments and a longitudinal axis of the stent which are perfectly reproducible after the step of fixing the tubular body in its diameter corresponding to the resting state.

According to an improved embodiment of the invention, after introducing the plaited tubular body into the aforementioned tube, at least one of the ends of the plaited body is allowed to protrude while flaring such that, after the aforementioned thermal setting treatment, the stent is fixed in the resting state, with flaring of at least one of its ends. In this embodiment, at least a portion of the stent may automatically assume a shape of a hyperboloid segment.

The invention will now be described in more detail in the following description of non-limiting embodiments and with reference to the attached drawings in which identical or similar elements have the same references.

DETAILED DESCRIPTION OF THE PREFERRED EMBODIMENTS

Figure 1:
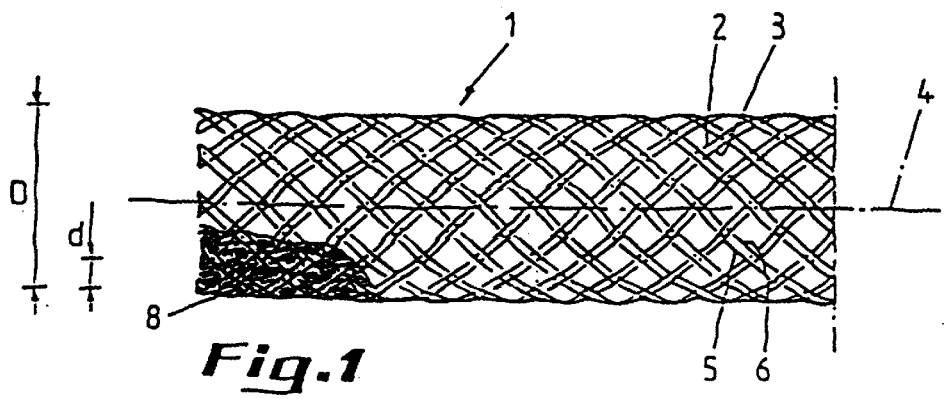
FIG. 1 represents a partially cut away side view of an end part of one embodiment of a self-expanding stent of the invention.

As can be seen from FIG. 1, the self-expanding stent according to the invention (partially illustrated) is formed by a tubular body 1 having a cylindrical shape at the illustrated end. The tubular body 1 is formed by plaited filaments. It comprises first filaments, for example 2 and 3, which are arranged side by side, there being two of them in this case, and which thus form first multiple filaments wound along a first helicoid direction around the longitudinal axis 4 of the tubular body. It also comprises second filaments 5 and 6 which are arranged side by side, there being two of them in this case, and which thus form second multiple filaments wound along a second helicoid direction opposite to the first. It is clear that three, four or more filaments may be provided, arranged side by side, in order to form a multiple filament according to the invention. It should also be noted that the filaments arranged side by side to form a multiple filament are contiguous over almost their entire length. It is only for reasons of clarity and readability of the figures that the filaments forming a multiple filament, such as the filaments 2 and 3 or 5 and 6, respectively, are represented slightly separated from each other.

Figure 2:
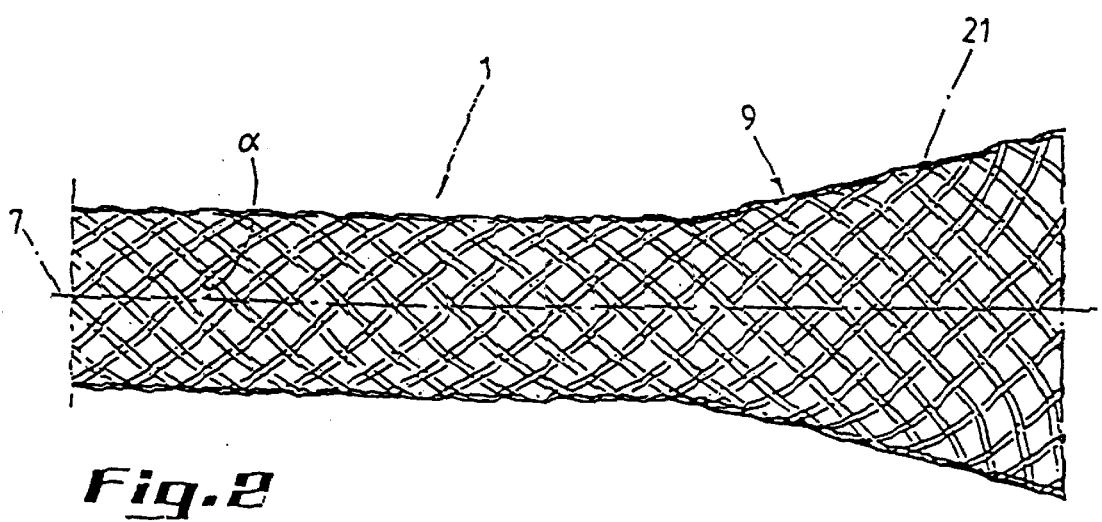
FIG. 2 represents a side view of an end part of a second embodiment of a stent according to the invention.
Figure 3:
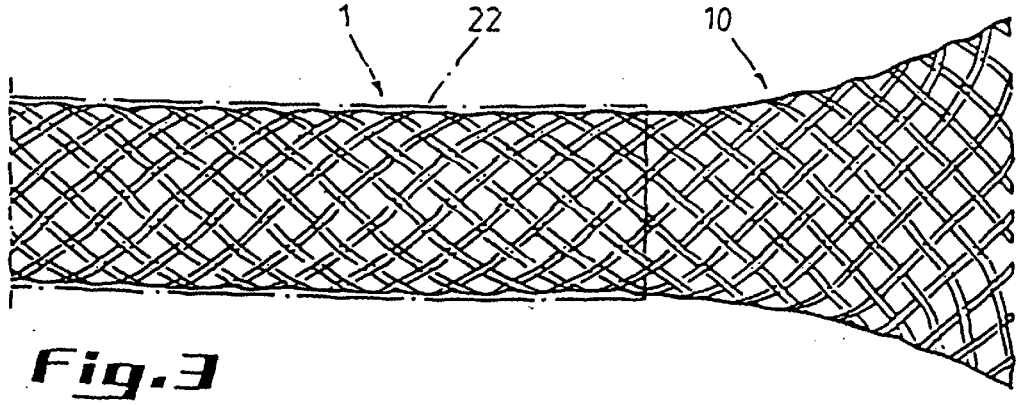
FIG. 3 represents a side view of an end part of a third embodiment of a stent according to the invention.

As can be seen in FIGS. 1–3, the multiple filaments of the tubular body 1 cross over according to a plaited arrangement, it being possible to vary the mode of plaiting as already indicated above.

The multiple filaments used consist of any material which is suitable for introduction into the human and animal body and which has sufficient rigidity and flexibility to produce a self-expanding stent. Biocompatible metallic filaments may, for example, be provided. Such filaments may be formed from, for example, stainless steel 3146 or wrought cobalt chromium nickel alloys satisfying standards ISO 5832/7 and/or ASTM F1058-9, ELIGILOY, NITINOL, or PHYNOX with AFNOR designation K13 C20 N16 Fe15 Do7, marketed by Sprint Metal, Paris, France. It is clear that other metallic filaments or filaments of other materials, for example plastics having elastic memory, may be used.

In FIG. 1, the tubular body is represented in the resting state. In this state it has, in this embodiment example, a diameter D of approximately 28 mm. Its length is chosen as a function of the use of the stent. In its compressed state, that is to say at the time when it will be required to be introduced in a known introducer (not shown) the stent will require a diameter d which may be as small as 3 to 4 mm. The compressed state is obtained by radial compression on the stent and/or by moving apart the ends of the stent in the axial direction. In the working state, the stent therefore has a length greater than its length in the resting state.

In this resting state the filaments have, in the embodiments illustrated, with respect to a longitudinal axis 7 (FIG. 2) of the stent, an angle of at most 45°, and preferably less than this value. This offers the great advantage that the stent, in the compressed state, inserted in its introducer, does not have an excessive length with all the release problems which this raises, as already indicated above. Such an angle of 45° is not, however, critical for the invention and may be exceeded according to the circumstances.

As can be seen in FIG. 1, the tubular body 1 may be lined on its internal surface with a covering 8. This covering may be made of any biocompatible material which is suitable, in particular, for the manufacture of luminal endoprostheses (see Patent #EP-A-0,603,959). A covering on the external surface may be provided instead of or in addition to the internal covering 8.

FIG. 2 illustrates a stent according to another embodiment of the invention where the tubular body 1 has a flaring 9 at one end. As can be seen at the flaring location, the multiple filaments follow a helix with increasing radii. The flaring 9 shown in FIG. 2 is of a frustoconical shape.

FIG. 3 illustrates a stent, the tubular body 1 of which has at one end a flaring 10 which has the shape of a hyperboloid segment. This flaring gives rise to one end 10 of the stent 1, in the shape of a truncated hyperboloid.

The embodiments having a flared end offer the great advantage of allowing good fixation of the stent during release, without subsequent migration in the cavity. Attachment or sealing to the wall of this cavity takes place much more intensely at the end which is released first, by virtue of its flared shape, and this end keeps the released device in the position which was given to it. A stent having two flared ends, each, in particular, in the shape of a truncated hyperboloid, proves very advantageous, in particular when introducing an endoprosthesis for treating an abdominal artery aneurysm. Its two ends match the shape of the necks of the aneurysm while thus perfectly retaining the endoprosthesis which is at this location subjected to the stresses due to blood pressure.

The truncated hyperboloid shape is also very well suited to treating subclavian artery aneurysms, in which the stent may be greatly bent at one end. Instead of being crushed by closing up at this end, as stents of the prior art, the stent remains in a largely open position at its end, by virtue of the shape of the latter.

Figure 4:
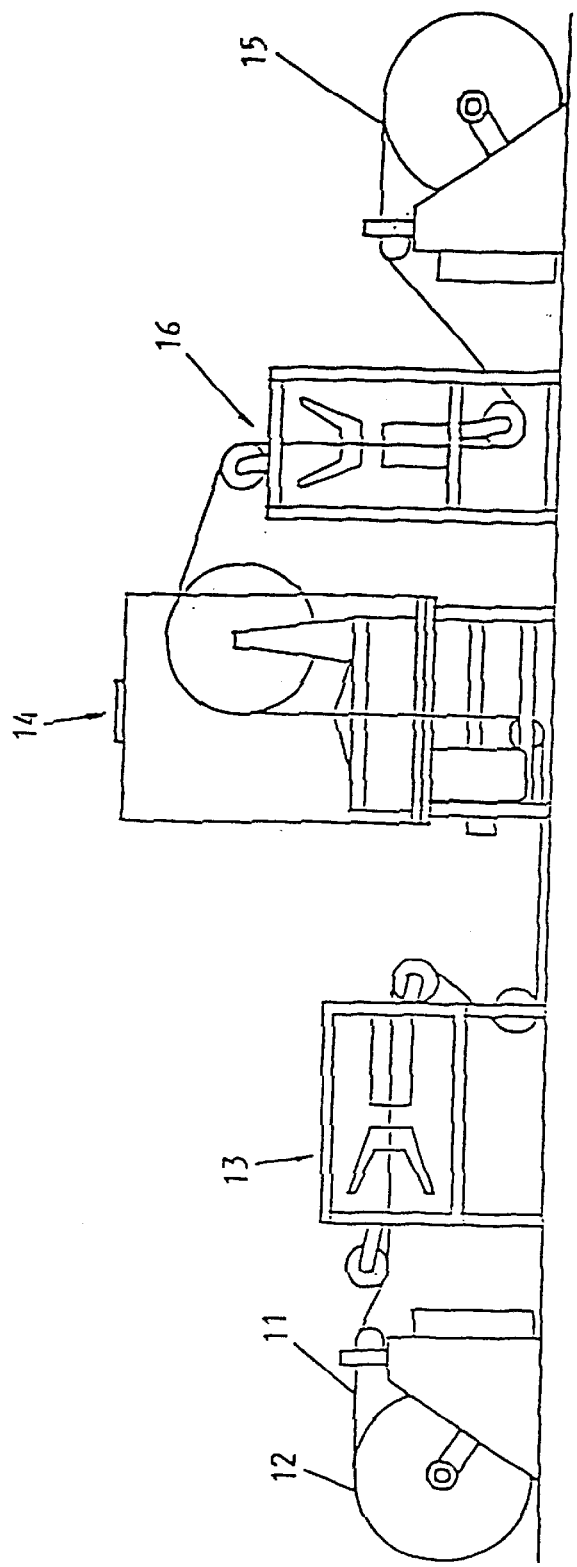
FIG. 4 represents a general diagram of the plaiting equipment used to make the stent of the invention.
Figure 5:
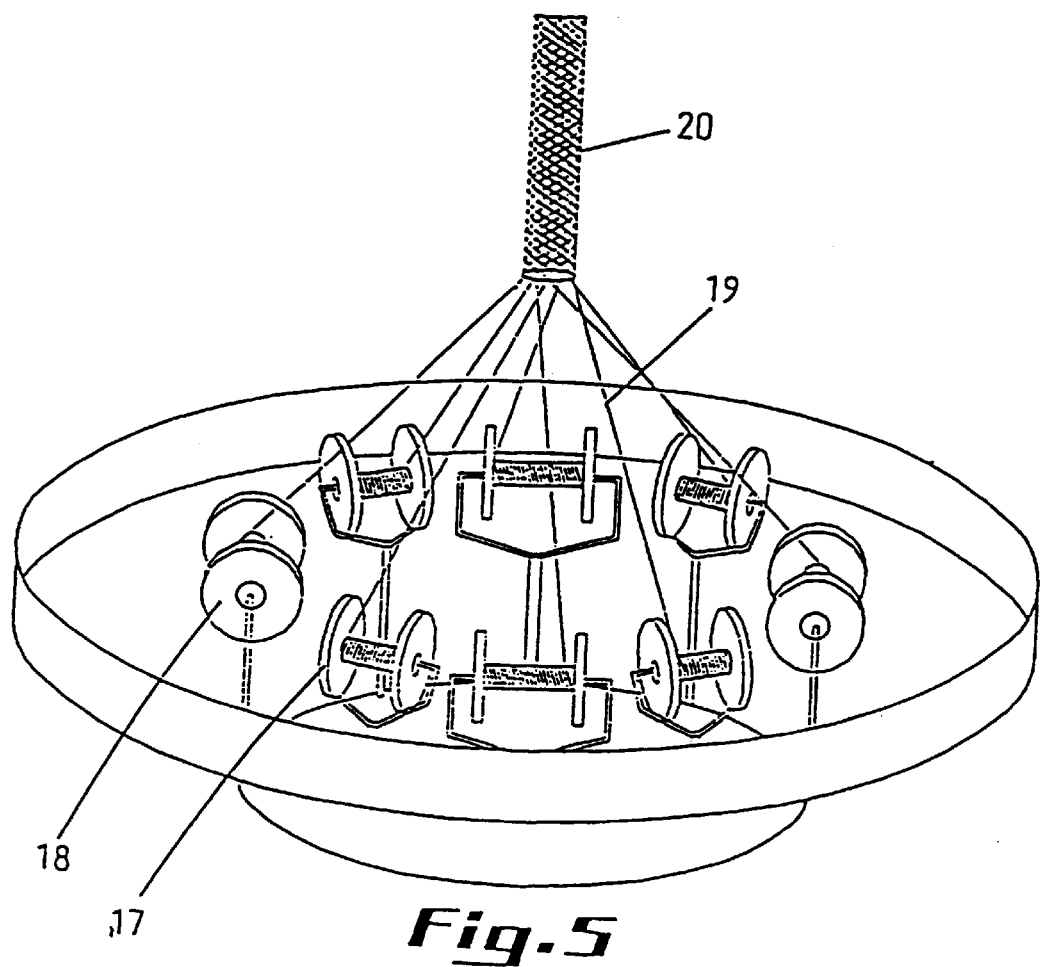
FIG. 5 represents a more detailed view of the plaiting operation according to the invention.

The manufacture of a plaited tubular body has been known for a long time in the technique of cable production, and use is made here of this technique which is illustrated in the attached FIGS. 4 and 5. In FIG. 4, a bearing cable 11 is unwound from a spool 12. A guidance system, denoted overall by the reference 13, guides and tensions this cable 11 which then passes through the plaiting machine 14 schematized here. It leaves this machine, provided with a plaited tubular body and is then wound onto a spool 15 after having been tensioned by a new guidance system 16.

The plaiting machine 14 used is represented in somewhat more detail in FIG. 5. As a plaiting machine of this type, use may, for example, be made of a DBH or DB model machine marketed by the firm Spiraltex, Meximieux, France. The reels or carriers of such a machine (only some of which have been represented) are divided into two groups, the reels 17 of one group rotating in the opposite direction to the reels 18 of the other group, about the axis of the plaited structure. The bearing cable 11, not represented here, passes vertically through the middle of the plaited structure.

According to the invention, and in contrast to the state of the art regarding manufacture of self-expanding stents, multiple filaments 19 are unwound from each or some of the reels. Moreover, prior to plaiting, a plurality of filaments were simultaneously wound onto at least some, and preferably all of the reels. As already stated, these multiple filaments originating from the reels are contiguous over almost their entire length. The choice of the number of reels depends on the diameter of the desired plaited structure 20.

Advantageously, the plaited tubular body has, after plaiting, a diameter slightly greater than the diameter (for example D) of the finished stent in the resting state. The plaited tubular body is then be removed from its bearing cable, and in a conventional manner, the plaited tubular body can then be placed over a mandrel (for example 21 in FIG. 2) which has the desired suitable shape. In FIG. 2, this mandrel therefore has the shape of a cylinder having, for example, diameter D, bearing a truncated cone at one end. The plaited tubular body is then subjected to a tension at its ends and to a thermal setting treatment which fixes the tubular body at the dimensions of the mandrel. After this treatment, in the resting state, the tubular body has a diameter D and has the shape illustrated in FIG. 2.

According to the invention, provision is also made, as a variant, to extend the plaited tubular body and to introduce it in a tube 22, represented in dots and dashes in FIG. 3, which has an internal diameter equal to the desired diameter of the finished stent. It is then subjected to the thermal setting treatment. For example, introduction of a tubular plaited structure with a diameter of 35 mm into a tube with an internal diameter of 28 mm may be envisaged. The filament undergoes setting at approximately 550° C. for 3 hours, under inert atmosphere (argon or nitrogen with 5% hydrogen) or under a vacuum of $10^{-5}$ to $10^{-8}$ torr. Following this treatment, if the plaited structure has been completely introduced in the tube 22, the finished stent has a cylindrical shape corresponding to that represented in FIG. 1. If, on the other hand, one or both ends of the plaited structure project out of the tube, these will automatically assume the shape of a truncated hyperboloid, as illustrated in FIG. 3. The great advantage of this operation is that the finished stents obtain an angle between the multiple filaments and a longitudinal axis which is, under the same treatment conditions, always identical and perfectly reproducible. This is in contrast to the prior art situation where the setting is accomplished on a mandrel.

The advantages of the invention will now be illustrated with the aid of nonlimiting comparative examples. The measurement method in these examples consists in evaluating the resistance of the stents to radial compression. A loop of a metallic filament with a diameter of 0.12 mm, attached at one end to a support, is passed around the stent to be examined, approximately in the middle of the latter. Various weights are then suspended from the other end of the filament and the diameter is then measured at the constriction obtained for each weight suspended from the measurement filament.

EXAMPLE 1

A comparison is made between two stents which are formed by the same number of filaments (40 single filaments and 40 double filaments, respectively) and which have approximately the same angle between the filaments and a longitudinal axis and the same diameter in the resting state. The filaments of the stents are the same and have been plaited under the same conditions.

The stent according to the prior art has, in the resting state, a diameter of 32.77 mm and an angle of 52° C. The stent according to the invention has, in the resting state, a diameter of 31.4 mm and an angle of 51°. Reduction in diameter (mm) of the stent as a function of the mass suspended from the measurement filament is as follows:

| Mass (g) | Double filament | Single filament |
|---|---|---|
| 0 | 31.40 | 32.77 |
| 5 | 31.03 | 31.34 |
| 10 | 30.77 | 30.56 |
| 20 | 30.56 | 29.19 |
| 30 | 27.94 | 27.61 |
| 50 | 26.10 | 22.87 |
| 100 | 20.90 | 12.68 |
| 150 | 15.39 | 8.23 |
| 180 | 11.99 | 3.38 |
| 200 | 7.99 | 3.13 |

These measurement results clearly show that, above 50 g, i.e., corresponding to physiological conditions in the arteries, much more favorable resistances are obtained with the double-filament stent.

EXAMPLE 2

A comparison is made between three stents which are formed with the same number of filaments (40 single filaments and 40 double filaments, respectively) and which have approximately the same diameter in the resting state. The angle of the filaments with respect to a longitudinal axis is 66° for the stent according to the prior art of the art; it is 49° for a stent X according to the invention; and it is 44° for a stent Y according to the invention.

In the resting state, the three stents examined have an identical length, that is to say approximately 10 cm. The stent according to the prior art and the stent Y were then introduced in a Balt introducer of type ID5 (5 mm internal diameter) of 50 cm length. The stent according to the prior art occupies a length of 44 cm therein and the stent Y occupies a length of 18 cm therein.

Reduction in the diameter of the stent as a function of the mass suspended from the measurement filament is as follows:

| | Double filament | | Single filament |
|---|---|---|---|
| Mass (g) | Stent X (49°) Measured diameter (mm) | Stent Y (44°) Measured diameter (mm) | Measured (66°) diameter (mm) |
| 0 | 27.50 | 27.30 | 27.50 |
| 5 | 27.22 | 26.98 | 27.30 |
| 10 | 27.00 | 26.59 | 27.10 |
| 20 | 25.37 | 26.31 | 25.33 |
| 30 | 24.80 | 25.12 | 25.04 |
| 50 | 22.58 | 23.46 | 23.50 |
| 100 | 16.76 | 15.74 | 16.20 |
| 150 | 12.92 | 12.75 | 11.73 |
| 180 | 9.40 | 8.36 | 9.02 |
| 200 | 7.16 | 6.19 | 5.60 |

This example clearly shows that a double-filament stent having a plaiting angle significantly less than that used in certain stents according to the prior art offers equivalent resistance to compression, without the release problems indicated above.

EXAMPLE 3

A comparison between three stents is made, one (stent C) of which is formed by 72 individually wound filaments, as in the prior art, and the other two of which are formed by 36 double filaments according to the invention. The stents A–C have a diameter in the resting state of 32 mm. The filaments of the stents A and B have an angle with respect to the longitudinal axis of 53.75° and 53.25°, respectively, and those of the stent C have an angle of 55°.

| Mass (g) | Reduced diameter mesaured (mm) | | | | | |
|---|---|---|---|---|---|---|
| | A(53.75) | % (A) | B(53.25) | % (B) | C(55) | % (C) |
| 0 | 32.86 | 0.000 | 33.49 | 0.000 | 32.99 | 0.000 |
| 10 | 32.10 | 2.307 | 32.23 | 3.762 | 32.41 | 1.752 |
| 20 | 31.14 | 5.229 | 31.43 | 6.151 | 31.25 | 5.269 |
| 30 | 29.76 | 9.428 | 30.93 | 7.644 | 30.47 | 7.633 |
| 50 | 27.56 | 16.124 | 28.91 | 13.676 | 29.24 | 11.362 |
| 70 | 26.12 | 20.506 | 26.65 | 20.242 | 27.17 | 17.637 |
| 100 | 23.54 | 28.358 | 24.63 | 26.456 | 23.98 | 27.307 |
| 130 | 20.27 | 38.310 | 21.29 | 36.429 | 20.05 | 39.220 |
| 150 | 17.58 | 46.497 | 19.61 | 41.445 | 19.43 | 41.100 |
| 170 | 17.02 | 48.201 | 18.45 | 44.909 | 16.37 | 50.376 |
| 200 | 16.18 | 50.758 | 16.77 | 49.925 | 12.59 | 61.835 |

This example clearly shows that an equivalent, if not better, compression resistance is obtained with the stents according to the invention in comparison with the stent manufactured according to the prior art. It should, however, be noted that, in order to manufacture the stent C, it was necessary to resort to equipment comprising a plaiting machine with 72 reels, which is exceptional (and expensive) and much more complex to manipulate. Such a machine is also bulky and much noisier. In contrast, the stents A and B can be manufactured on the same plaiting machines as those used to date (for example with 36 reels).

It should be understood that the present invention is in no way limited to the forms and embodiments described hereinabove and that modifications may certainly be made thereto without departing from the scope of the appended claims.

I claim:

1. A self-expanding stent for introduction into a human or animal body, comprising:

a tubular body (1) which is radially expansible and retractable between a first diameter (d), corresponding to a compressed state of said stent, and a second diameter (D), greater than said first diameter (d), corresponding to a resting state of said stent, and is axially expansible and retractable between a first length, corresponding to said compressed state, and a second length, less than said first length, corresponding to said resting state, said tubular body being formed by plaited filaments (2, 3, 5, 6), with a first plurality of said plaited filaments (2, 3) being arranged adjacently side by side substantially continuously along substantially their entire lengths in a number at least equal to two and forming first multiple filaments (2, 3) wound along a first helicoid direction around a longitudinal axis (4) of the tubular body (1), and a second plurality of said plaited filaments (5, 6) being arranged adjacently side by side substantially continuously along substantially their entire lengths in a number at least equal to two and forming second multiple filaments (5, 6) wound along a second helicoid direction opposite to said first helicoid direction, each multiple filament wound in one of the said helicoid directions crossing multiple filaments wound in the other helicoid direction according to a plaited arrangement, wherein all of said first multiple filaments together cross all of said second multiple filaments on the same side of said second multiple filaments, and said first multiple filaments are not twisted around one another and said second multiple filaments are not twisted around one another.

2. A stent according to claim 1, wherein:
said tubular body formed by plaited multiple filaments has at least partially a cylindrical shape.

3. A stent according to claim 1, wherein:
said tubular body has at least at one of its ends, in the resting state, a flaring (9, 10) in which said multiple filaments follow a helix with increasing radii.

4. A stent according to claim 3, wherein:
said tubular body has a flaring at least at one of its ends which provides a substantially hyperboloid segment.

5. A stent according to claim 3, wherein:
said tubular body includes multiple filaments oriented at an angle ($\alpha$) of at most 45° with respect to a longitudinal axis of said tubular body.

6. A stent according to claim 5, further comprising:
an expandable graft covering (8) on at least one of an inside and an outside surface of said tubular body.

7. A stent according to claim 1, wherein:
said tubular body includes multiple filaments oriented at an angle ($\alpha$) of at most 45° with respect to a longitudinal axis of said tubular body.

8. A stent according to claim 1, further comprising:
an expandable graft covering (8) on at least one of an inside and an outside surface of said tubular body.

9. A stent according to claim 8, wherein:
said multiple filaments are comprised of biocompatible metallic filaments.

10. A stent according to claim 1, wherein:
said multiple filaments are comprised of biocompatible metallic filaments.

* * * * *